United States Patent [19]

Reifschneider et al.

[11] Patent Number: 4,568,670
[45] Date of Patent: Feb. 4, 1986

[54] N'-(METHOXY(METHYLTHIO)PHOSPHINYL)-N,N-DIMETHYL CARBAMIMIDOTHIOIC ACID, ETHYL ESTER

[75] Inventors: Walter Reifschneider, Walnut Creek; Doris L. Paroonagian, Pleasant Hill, both of Calif.

[73] Assignee: The Dow Chemical Company, Midland, Mich.

[21] Appl. No.: 490,692

[22] Filed: May 2, 1983

Related U.S. Application Data

[63] Continuation-in-part of Ser. No. 399,102, Jul. 16, 1982.

[51] Int. Cl.$^4$ .......................... A01N 57/28; C07F 9/24
[52] U.S. Cl. ........................................ 514/118; 260/944
[58] Field of Search ..................... 260/944; 424/211; 514/118

[56] References Cited

U.S. PATENT DOCUMENTS 4,237,124 12/1980 Hoffmann et al. ................... 424/211

FOREIGN PATENT DOCUMENTS 172676 5/1978 Czechoslovakia .

Primary Examiner—Anton H. Sutto
Attorney, Agent, or Firm—S. Preston Jones; Ronald G. Brookens

[57] ABSTRACT

N'-(Methoxy(methylthio)phosphinyl)-N,N-dimethyl carbamimidothioic acid, ethyl ester is employed as an insecticide and particularly plant systemic insecticides for the control of sucking and boring-type insects which attack plants of economic importance.

4 Claims, No Drawings

N'-(METHOXY(METHYLTHIO)PHOSPHINYL)-N,N-DIMETHYL CARBAMIMIDOTHIOIC ACID, ETHYL ESTER

REFERENCE TO RELATED APPLICATION

This application is a continuation-in-part of Ser. No. 399,102, filed July 16, 1982.

DESCRIPTION OF PRIOR ART

Various phosphorus derivatives of carbamimidothioic acid esters are known such as those taught in Czechoslovakian Pat. No. 172,676. In addition, these compounds are taught to have pesticidal activity.

SUMMARY OF THE INVENTION

The present invention is directed to the compound N'-(methoxy(methylthio)phosphinyl)-N,N-dimethyl carbamimidothioic acid, ethyl ester, which corresponds to the formula

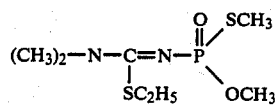

In addition, the present invention is also directed to insecticidal compositions containing the above compound as the active insecticide and the use of such compositions for the kill and control of sucking and boring-type insects which attack a variety of plants such as rice, cotton, corn, vegetables and fruit and nut trees.

The active compound of the present invention is an oil and is soluble in many common organic solvents. The compound has also been found to have unexpectantly low mammalian and fish toxicity.

In addition, the active compound of the present invention has been found to be highly effective as a plant systemic insecticide and acaricide for the kill and control of planthoppers, leafhoppers, aphids, phytophagous mites and other sucking insects, in particular those sucking insects which attack rice plants.

The compound of the present invention can be prepared by a variety of methods as follows:

Method A

The compound can be prepared by the rearrangement of the isomeric N'-(dimethoxyphosphinothioyl)-N,N-dimethylcarbamimidothioic acid, ethyl ester with the aid of methyl iodide.

The reaction scheme is as follows:

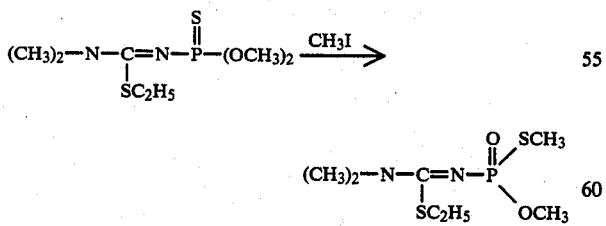

No attempt is being made in this or any subsequent reaction scheme to present a balanced equation.

In carrying out this reaction, one mole of N'-(dimethoxyphosphinothioyl)-N,N-dimethylcarbamimidothioic acid, ethyl ester, the solvent and from 0.1 to 12 moles of methyl iodide are mixed together in any convenient manner. The mixture is then stirred at a temperature between 15° C. and gentle reflux until the rearrangement is complete. Depending on the amount of methyl iodide employed, rearrangement is complete in 30 minutes to approximately 50 hours.

Representative solvents include, for example, methanol, acetonitrile, methylene chloride, tetrahydrofuran, benzene, toluene, cyclohexane and the like. Excess methyl iodide may also be employed as solvent.

Method B

N'-(Methoxy(methylthio)phosphinyl)-N,N-dimethylcarbamimidothioic acid, ethyl ester can also be prepared by thermal rearrangement of the isomeric N'-(dimethoxyphosphinothioyl)-N,N-dimethylcarbamimidothioic acid, ethyl ester.

The reaction scheme is as follows:

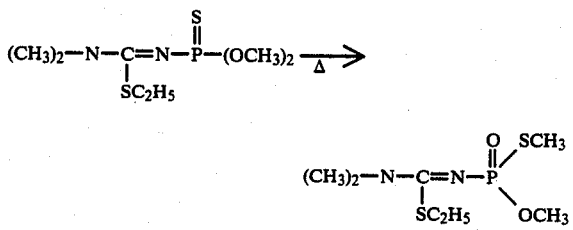

In carrying out this reaction N'-(dimethoxyphosphinothioyl)-N,N-dimethylcarbamimidothioic acid, ethyl ester is distilled repeatedly at a temperature from about 140° C. to about 190° C. and a reduced pressure from about 0.3 to about 1.5 millimeters of mercury.

Method C

Substantially equimolar amounts of N,N-dimethylcarbamimidothioic acid, ethyl ester of the formula

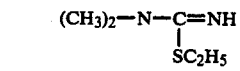

and phosphorochloridothioic acid, O,S-dimethyl ester of the formula

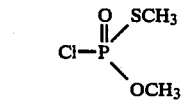

are reacted together in the presence of a solvent and a HCl acceptor.

The reaction scheme is as follows:

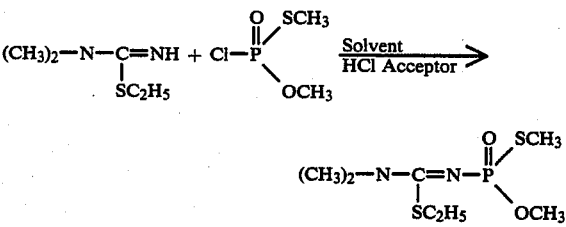

In carrying out this reaction, the N,N-dimethylcarbamimidothioic acid, ethyl ester and the phosphorus chloride reactants, the solvent and the HCl acceptor are mixed together in any convenient manner. The mixture is then stirred at a temperature between 15° C. and gentle reflux until all of the reactants are consumed.

Representative solvents include, for example, acetonitrile, methylene chloride, cyclohexane, benzene, toluene, xylene, acetone, methyl ethyl ketone, diethyl ether, dioxane, tetrahydrofuran and the like.

Representative hydrogen chloride acceptors (acid binding agents) include for example, alkali metal carbonates such as sodium and potassium carbonate and tertiary amines such as, for example, triethylamine, pyridine and the like.

At the completion of the reaction, the reaction mixture is filtered to remove any insolubles and the filtrate concentrated under reduced pressure. The residue is then taken up in diethyl ether, benzene, toluene, methylene chloride or chloroform and washed thoroughly with water and then with a saturated sodium chloride solution and dried. The solvent is removed by evaporation under reduced pressure leaving the desired product.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

A.

N'-(Methoxy(methylthio)phosphinyl)-N,N-dimethyl-carbamimidothioic acid, ethyl ester

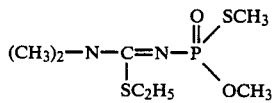

A mixture of 25.0 grams (g) of N'-dimethoxyphosphinothioyl)-N,N-dimethylcarbamimidothioic acid, ethyl ester and 150 g of methyl iodide was heated under gentle reflux for 6 hours. The methyl iodide was then removed by distillation and the residue was exhaustively extracted with hexane. The hexane solution was treated with charcoal, filtered and the filtrate concentrated in a rotary evaporator, leaving 12.9 g (52 percent (%) of theoretical) of the N'-(methoxy(methylthio)-phosphinyl)-N,N-dimethylcarbamimidothioic acid, ethyl ester product as a colorless oil. The product has a refractive index of $n_d^{25} = 1.5598$.

Analysis: Found: C, 32.61; H, 6.46; N, 11.00. Calculated for $C_7H_{17}N_2O_2PS_2$: C, 32.80; H, 6.69; N, 10.93.

B. The above product was also prepared by an alternative procedure

A mixture of 36.8 g of N'-(dimethoxyphosphinothioyl)-N,N-dimethylcarbamimidothioic acid, ethyl ester, 120 ml of methanol and 5.0 g of methyl iodide was heated under reflux for 18 hours, then another 5.0 g of methyl iodide was added and heating under reflux was continued for 6 hours. The mixture was concentrated under vacuum, the residue dissolved in methylene chloride, the methylene chloride solution washed once with water and dried over anhydrous magnesium sulfate. The solvent was removed in a rotary evaporator and the residual oil distilled in a Kugelrohr (bath temperature 140° C., pressure 0.3 mm) yielding 23.8 g (65% of theoretical) of N'-(methoxy(methylthio)phosphinyl)-N,N-dimethylcarbamimidothioic acid, ethyl ester. The IR and NMR spectra are in agreement with the assigned structure and identical to those obtained from the compound prepared by the method A.

C. The above product was also prepared by an alternative procedure

To a mixture of 6.6 g of N,N-dimethylcarbamimidothioic acid, ethyl ester, 8.0 g of finely powdered potassium carbonate and 50 ml of acetonitrile was added dropwise 8.0 g of phosphorochloridothioic acid, O,S-dimethyl ester. The mixture was stirred until no starting material could be detected by GLC (Gas Liquid Chromatography). The salts were then removed by filtration, the filtrate concentrated under vacuum, the residue taken up in ether, the ether solution washed once with water, once with 5% aqueous sodium hydroxide, once with saturated sodium chloride solution and dried over anhydrous magnesium sulfate. The solvent was removed under vacuum and the residue distilled in a Kugelrohr (bath temperature 140° C., pressure 0.3 mm) yielding 8.2 g (64% of theoretical) of N'-(methoxy(methylthio)phosphinyl)-N,N-dimethylcarbamimidothioic acid, ethyl ester as a colorless oil. The IR and NMR spectra are identical to those obtained from the compound prepared by method A.

The compound of the present invention is very effective for the control of the many sucking and boring-type insects found on the roots or aerial portions of growing plants.

Representative of the various sucking or boring-type insects which attack plants and which are killed and controlled by the active compound employed in the present invention are members of the orders Homoptera, Thysanoptera, Hemiptera, Coleoptera, and Acarina. More specifically, kill and control is obtained for insects such as aphids (Aphididae) such as the green peach aphid (*Myzus persicae*), the bean aphid (*Aphis fabae*), the black cherry aphid (*Myzus ceraci*), the pea aphid (*Acythorsiphum pisum*) and the potato aphid (*Macrosiphum euphorbiae*), the currant gall aphid (*Cryptomyzus ribis*), the mealy apple aphid (*Sappaphis mali*), the mealy plum aphid (*Hyalopterus pruni*), the cotton aphid (*Aphis gossypii*); the whiteflies (Aleyrodidae) including the banded wing whitefly (*Trialeurodes abutilonea*), grape whitefly (*Trialeurodes vittata*), greenhouse whitefly (*Trialeurodes vaporarium*) and sweet potato whitefly (*Bemisia tabacii*); scales such as the San Jose scale (*Aspidiotus perniciosus*), oyster scale (*Lepidosaphes ulnii*), the California red scale (*Aonidiella aurantii*), black scale (*Saissetia olea*) Terapin scale (Lecanium sp) and the oleander scale (*Aspidiotus hederae*); mealybugs (coccidae) such as the grape mealybug (*Pseudococcus maritimus*), greenhouse mealybug (Pseudococcus sp) and citrus mealybug (Planococcus sp); thrips (Thysanoptera) such as (*Hercinothrips femoralis*), gladiolus thrips (Taeniothrips sp), onion thrips (*Thrips tabacii*), greenhouse thrips (Heliothrips sp), flower thrips (Frankliniella sp) and rice thrips (*Chloethrips oryzae*); bugs, for example the beet bug (*Piesma quadrata*), squash bug (Anasa sp), harlequin bugs (*Murgantia histrionica*), (Trigonotylus sp), Corbett ricebug (*Leptocorixa corbetti*), slender ricebug (*Cletus trigonus*), black ricebug (*Scotinophora lurida*), Plant bugs (Lygus sp), fleahoppers (Halticus sp), cotton fleahoppers (Psallus sp), the cotton bug (*Dysdercus intermedius*) and stinkbugs such as the southern green stinkbug (*Nezara viridulla*); leafhoppers and planthoppers, such as aster leafhopper (*Macrosteles fascifrons*), rice green leafhopper (*Nephotettix virescens*), zig zag leafhopper (*Recilia dorsalis*), (*Nephotettix apicalis*), white back planthopper (*Sogattella furcifera*), brown planthopper (*Nilaparvata lugens*), smaller brown planthopper (*Laodelphax striatellus*), grape leafhopper (Erythroneura sp), potato leafhopper (*Empoasca fabae*), apple sucker (*Psylla mali*), pear psylla (*Psylla pyricola*), potato psillid (*Paratrioza cockerlelli*) and the like as well and rice water weevil (*Lissorhoptrus oryzophilus*); the mites (Acarina) in particular, the spider mites (Tetranychidae) such as the two-spotted spider mite (*Tetranychus urticae*), carmine spider mite (*Tetranychus cinnabarinus*) and the European red mite (*Panonychus ulmi*), blister mites, for example the currant blister mite (*Eriophyes ribis*) and tarsonemids, for example the broad mite (*Hemitarsonemus latus*), the cyclamen mite (*Tarsonemus pallidus*); borers such as the rice stemborer (Chilo sp), pink borer (Sesamia sp) and the paddy borer (Tryporyza sp); and the like.

In the present specification and claims, the term "systemic" defines the translocation of the active compound employed in the present method through the plant. The active compound can be applied either to the above-ground or preferably to below-ground portions of the plant.

The application of an insecticidally effective amount of the active compound of the present invention is critical to the method of the present invention. The active compound can sometimes be employed in unmodified form. Frequently, however, for easier application, the compound is modified by the employment with it of an adjuvant or inert carrier therefor. Thus, for example, the present compound is relatively soluble in water and is also relatively soluble in oils, including plant essential oils. Therefore, the practical enjoyment of the beneficial utilities of the present compound often requires that the compound be composited with one or more adjuvant substances which are chemically inert to the active compound, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the active compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising the presently claimed compound, an organic liquid as a solvent and carrier therefor, and a propellant material. Numerous other embodiments will become available to those skilled in the art in view of the teachings set forth hereinbelow.

The exact concentration of the active compound in a composition thereof with an adjuvant therefor can vary; it is only necessary that the active compound be present in a sufficient amount so as to make possible the application of an insecticidally effective dosage. Generally, for practical applications, the active compound can be broadly applied to the plants or to the soil around the roots of the plants or to water, such as in broadcast rice paddy applications in compositions containing from about 0.00001 percent to about 98 percent by weight of the active compound.

In preparation of dust compositions, the product can be compounded with any of the finely divided carrier solids such as prophyllite, diatomaceous earth, gypsum and the like. In such operations, the finely divided carrier is ground or mixed with the active compound, as active agent, or wetted with a solution of the active agent in a volatile organic solvent. Similarly, dust compositions containing the active product can be similarly compounded from various of the solid dispersing agents, such as fuller's earth, attapulgite and other clays. These dusts compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, the active compound or a dust concentrate composition containing said compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the active compound can be compounded with a suitable water-immiscible organic liquid and a surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene liquid halohydrocarbons and synthetic organic oils. The surface-active dispersing agents are usually employed in liquid compositions in the amount of from 0.1 to 20 percent by weight of the combined weight of the dispersing agent and active compound.

When operating in accordance with the present invention, the active compound or a composition containing the active compound is applied to the plants or to their habitat in any convenient manner, for example, by means of hand dusters or sprayers. Application to the foliage of the plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane.

In further embodiments, the compound of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compound. Accordingly, in such embodiments, the pesticidal compound is employed as a supplemental toxicant for the same or for a different pesticidal use, or as an additament. The compounds in combination can generally be present in the ratio of from about 1 to about 99 parts of the compound of the present invention with from about 99 to about 1 part of the additional compound(s).

Dosage amounts are generally from 15–1,000 grams (g) preferably from 40–600 g of active compound and most preferably from 125–500 g of active compound per hectare. However, in special cases, it is possible to exceed or reduce the amount and this may sometimes be necessary.

EXAMPLE II

Aqueous dispersions were prepared by admixing the compound of the present invention, dissolved in a suitable inert solvent, with a predetermined quantity of water and a predetermined amount of a surfactant to give aqueous dispersions containing varying predetermined amounts of one of the compounds as the sole toxicant.

Separate rice plants were dipped into one of the dispersions and permitted to dry.

A plastic cylinder was placed around each of the plants and 10 adult Aster leafhoppers were placed in the cylinder and the cylinder capped. In a like manner, 10 adult Aster leafhoppers were placed on control plants which had been dipped in a solution containing only water and surfactant. The plants were maintained under conditions conducive to the growth of the plants and leafhoppers. After a period of three days, the cylinder and plants were examined to determine the percent control at the various concentrations of the toxicant applied. The percent control is determined by the number of dead leafhoppers versus the number of leafhoppers (10) with which the plants were infested.

To determine residual control, the plants were reinfested with an additional 10 adult Aster leafhoppers after a period of 7 and 14 days. Percent control was determined as described above.

The results of these examinations are set forth below in Table I.

TABLE I

Control of the Aster Leafhopper by Foliar Application of Insecticide to Rice

| Compound | Days After Treatment | Percent Control at Indicated Dosage (ppm) | | | | | |
|---|---|---|---|---|---|---|---|
| | | 400 | 100 | 25 | 6.5 | 1.5 | 0.38 |
| (CH$_3$)$_2$—N—C=N—P(=O)(SCH$_3$)(OCH$_3$) with SC$_2$H$_5$ | 0 | 100 | 100 | 100 | 88 | 55 | 0 |
| | 7 | 100 | 75 | 8 | 6 | 0 | 0 |
| | 14 | 20 | 0 | 0 | 0 | 0 | 0 |
| Control | 0 | 0 | | | | | |
| | 7 | 0 | | | | | |
| | 14 | 0 | | | | | |

EXAMPLE III

Aqueous dispersions were prepared by admixing the compound of the present invention, dissolved in a suitable inert solvent, with a predetermined quantity of water and a predetermined amount of a surfactant to give aqueous dispersions containing varying predetermined amounts of the compound as the sole toxicant.

Separate rice plants were treated by adding a predetermined amount of one of the test dispersions to the root of the plant to determine systemic activity.

A plastic cylinder was placed around each of the plants and 10 adult Aster leafhoppers were placed in the cylinder and the cylinder capped. In a like manner, 10 adult Aster leafhoppers were placed on control plants which were treated at the root zone with a solution containing only water and surfactant. The plants were maintained under conditions conducive to the growth of the plants and leafhoppers. After a period of three days, the cylinder and plants were examined to determine the percent control at the various concentrations of the toxicant applied. The percent control is determined by the number of dead leafhoppers versus the number of leafhoppers (10) with which the plants were infested.

To determine the residual control, the plants were reinfested with an additional 10 adult Aster leafhoppers after a period of 7 and 14 days. Percent control was determined as described above.

The results of these examinations are set forth below in Table II.

TABLE II

Control of the Aster Leafhopper by Root Systemic Application of Insecticide to Rice

| Compound | Days After Treatment | Percent Control at Indicated Dosage (ppm) | | | | | |
|---|---|---|---|---|---|---|---|
| | | 400 | 100 | 25 | 6.5 | 1.5 | 0.38 |
| (CH$_3$)$_2$—N—C=N—P(=O)(SCH$_3$)(OCH$_3$) with SC$_2$H$_5$ | 0 | 100 | 100 | 100 | 100 | 100 | 0 |
| | 7 | 100 | 100 | 100 | 100 | 100 | 40 |
| | 14 | 100 | 100 | 100 | 64 | 6 | 0 |

TABLE II-continued
Control of the Aster Leafhopper
by Root Systemic Application of Insecticide to Rice

| Compound | Days After Treatment | Percent Control at Indicated Dosage (ppm) | | | | | |
|---|---|---|---|---|---|---|---|
| | | 400 | 100 | 25 | 6.5 | 1.5 | 0.38 |
| Control | 0 | 0 | | | | | |
| | 7 | 0 | | | | | |
| | 14 | 8 | | | | | |

EXAMPLE IV

Aqueous dispersions were prepared by admixing the compound of the present invention, dissolved in a suitable inert solvent, with a predetermined quantity of water and a predetermined amount of a surfactant to give aqueous dispersions containing varying predetermined amounts of the compound as the sole toxicant.

Rice seedlings were grown in soil using containers without drain holes. After emergence, the pots were flooded and the water level was maintained above the soil line throughout the experiment to simulate rice paddy like conditions.

Separate rice plants were treated by adding a predetermined amount of one of the test dispersions to the paddy water.

A plastic cylinder was placed around each of the plants and 10 adult Aster leafhoppers were placed in the cylinder and the cylinder capped. In a like manner, 10 adult Aster leafhoppers were placed on control plants which were treated at the root zone with a solution containing only water and surfactant. The plants were maintained under conditions conducive to the growth of the plants and leafhoppers. After three days, the cylinders and plants were examined to determine the percent control at the various concentrations of the toxicant applied. The percent control is determined by the number of dead leafhoppers versus the number of leafhoppers (10) with which the plants were infested.

The results of this examination is set forth below in Table III.

TABLE III
Control of the Aster Leafhopper on Rice
with a Broadcast Application of
Insecticide to the Paddy Water

| Compound | Days After Treatment | Percent Control at Indicated Dosage (Kg a.i./hectare) | | | |
|---|---|---|---|---|---|
| | | 0.5 | 0.25 | 0.125 | 0.06 |
| $(CH_3)_2-N-C=N-P\begin{subarray}{c}O\\ \parallel\end{subarray}\begin{subarray}{c}SCH_3\\ OCH_3\end{subarray}$ with $SC_2H_5$ | | 0 | 100 | 90 | 74 | 9 |
| Control | | 0 | 0 | | | |

EXAMPLE V

Aqueous dispersions were prepared by admixing the compound of the present invention, dissolved in a suitable inert solvent, with a predetermined quantity of water and a predetermined amount of a surfactant to give aqueous dispersions containing varying predetermined amounts of the compound as the sole toxicant.

Separate cotton plants were infested with 20 two-spotted spider mites and the plants sprayed with one of the dispersions to run off. In a like manner, 20 two-spotted spider mites were placed on control plants and the plants sprayed to run off with a solution containing only water and surfactant. The plants were maintained under conditions conducive to the growth of the plants and mites. After a period of five days, the plants were examined to determine the percent control at the various concentrations of the toxicant applied. Percent control is determined by the number of mobile mites on the test plants versus the number of mobile mites on the control plants.

The results of this examination is set forth below in Table IV.

TABLE IV
Control of the Two-Spotted Spider Mite,
*Tetranychus urticae*, by Foliar
Application of Insecticide to Cotton

| Compound | Percent Control At Indicated Dosage (ppm) | | |
|---|---|---|---|
| | 400 | 100 | 25 |
| $(CH_3)_2-N-C=N-P\begin{subarray}{c}O\\ \parallel\end{subarray}\begin{subarray}{c}SCH_3\\ OCH_3\end{subarray}$ with $SC_2H_5$ | 90 | 75 | 50 |
| Control | 0 | | |

EXAMPLE VI

Aqueous dispersions were prepared by admixing the compound of the present invention, dissolved in a suitable inert solvent, with a predetermined quantity of water and a predetermined amount of a surfactant to give aqueous dispersions containing varying predetermined amounts of the compound as the sole toxicant.

Separate cotton plants were infested with 20 two-spotted spider mites and a predetermined volume of the test dispersion was injected into the root zone of the plants to determine systemic insecticidal effects. In a like manner, 20 two-spotted spider mites were placed on control plants and a solution containing only water and surfactant was injected into the root zone. The plants were maintained under conditions conducive to the growth of the plants and mites. After a period of five days, the plants were examined to determine the percent control at the various concentrations of the toxicant applied. Percent control is determined by the number of mobile mites on the test plants versus the number of mobile mites on the control plants.

The results of this examination is set forth below in Table V.

TABLE V

Control of the Two-Spotted Spider Mite, *Tetranychus urticae*, by Root Systemic Application of Insecticide to Cotton

| Compound | Percent Control At Indicated Dosage (ppm) | | |
|---|---|---|---|
| | 400 | 100 | 25 |
| $(CH_3)_2-N-C(SC_2H_5)=N-P(=S)(SCH_3)(OCH_3)$ | 100 | 90 | 50 |
| Control | 0 | | |

EXAMPLE VII

Aqueous dispersions were prepared by admixing the compound of the present invention, dissolved in a suitable inert solvent, with a predetermined quantity of water and a predetermined amount of a surfactant to give aqueous dispersions containing varying predetermined amounts of the compound as the sole toxicant.

Separate cotton plants were infested with several hundred one week old, banded-wing whitefly nymphs. Plants were sprayed to run off with each of the dispersions. In a like manner several hundred nymphs were infested onto a control plant and the plants sprayed to run off with a solution containing only water and surfactant. The plants were maintained under conditions conducive to the growth of the plants and insects. After a period of 21 days, the plants were examined to determine the percent control at the various concentrations of the toxicant applied. Percent control was determined by the number of nymphs which did not successfully emerge as adults. The results of this examination are set forth below in Table VI.

TABLE VI

Control of Banded-Wing Whitefly Nymphs *Trialeurodes abutilonea*, by Foliar Application of Insecticide to Cotton

| Compound | Percent Control at Indicated Dosage (PPM) | | |
|---|---|---|---|
| | 400 | 100 | 25 |
| $(CH_3)_2-N-C(SC_2H_5)=N-P(=O)(SCH_3)(OCH_3)$ | 100 | 75 | 0 |
| Control | 0 | | |

EXAMPLE VIII

Aqueous dispersions were prepared by admixing the compound of the present invention, dissolved in a suitable inert solvent, with a predetermined quantity of water and a predetermined amount of surfactant to give aqueous dispersions containing varying predetermined amounts of the compound as the soil toxicant.

Separate cotton plants were infested with several hundred one week old banded-wing whitefly nymphs and a predetermined volume of this test dispersion was injected into the root zone of the plants to determine systemic insecticidal effects. In like manner, several hundred nymphs were infested onto control plants and a solution containing only water and surfactant was injected into the root zone. The plants were maintained under conditions conducive to the growth of the plants and whitefly nymphs. After a period of 21 days, the plants were examined to determine the percent control at the various concentrations of the toxicant applied. Percent control was determined by the number of nymphs which did not successfully emerge as adults. The results of this examination are set forth below in Table VII.

TABLE VII

Control of Banded-Wing Whitefly Nymphs, *Trialeurodes abutilonea*, by Root Systemic Application of Insecticide to Cotton

| Compound | Percent Control at Indicated Dosage (PPM) | | | |
|---|---|---|---|---|
| | 400 | 100 | 25 | 6.2 |
| $(CH_3)_2-N-C(SC_2H_5)=N-P(=O)(SCH_3)(OCH_3)$ | 100 | 100 | 95 | 0 |
| Control | 0 | | | |

EXAMPLE IX

Aqueous dispersions were prepared by admixing the compound of the present invention, dissolved in a suitable inert solvent, with a predetermined quantity of water and a predetermined amount of surfactant to give aqueous dispersions containing varying predetermined amounts of the compound as the sole toxicant.

Separate corn plants were infested with several hundred adults and nymphs of the corn leaf aphid, *Aphis maidis*, plants were sprayed to run off with each of the dispersions. In a like manner several hundred aphids were infested onto a control plant and the plants sprayed to run off with a solution containing only water and surfactant. The plants were maintained under conditions conducive to the growth of the plants and insects. After a period of seven days, the plants were examined for percent control at the various concentrations of the toxicant applied. Percent control is determined by the number of live aphids on the test plants versus the number of live aphids on the control. The results of this examination are set forth below in Table VIII.

TABLE VIII

Control of the Corn Leaf Aphid, *Aphis maidis*, by Foliar Application of the Insecticide to Corn

| Compound | Percent Control at Indicated Dosage (PPM) | | | |
|---|---|---|---|---|
| | 400 | 100 | 25 | 6.2 |
| $(CH_3)_2N-C(SC_2H_5)=N-P(=O)(OCH_3)(SCH_3)$ | 100 | 90 | 50 | 0 |
| Control | 0 | | | |

EXAMPLE X

Aqueous dispersions were prepared by admixing the compound of the present invention, dissolved in a suitable inert solvent, with a predetermined quantity of water and a predetermined amount of surfactant to give aqueous dispersions containing varying predetermined amounts of the compound as the sole toxicant.

Separate cotton plants were infested with several hundred adults and nymphs of the cotton aphid, *Aphis*

*gossipiella*. The aphids were confined to the underside of leaves by placing a ring of Vaseline ® around the circumference of the underside of leaf. One milliliter of each of the dispersions was sprayed onto the upper side of each of the test plants, taking care in not exposing aphids on the underside of leaf to the direct spray. In a like manner, several hundred nymphs were infested onto a control plant and a ring of Vaseline ® placed around the circumference of the underside of the leaf. The control plants were sprayed using a solution containing only water and surfactant. The plants were maintained under conditions conducive to the growth of the plants and insects. After a period of 12 days, the plants were examined to determine the percent control at the various concentrations of the toxicant applied. Percent control was determined by the number of aphids on the test plants versus the number of live aphids on the control. The results of this examination are set forth below in Table IX.

TABLE IX

Tanslaminar Control of the Cotton Aphid
*Asphis gossipiella*, on Cotton

| Compound | Percent Control at Indicated Dosage (PPM) | | |
|---|---|---|---|
| | 400 | 100 | 25 |
| CH₃\\N—C=N—P(=O)(SCH₃)(OCH₃) / CH₃ / SC₂H₅ | 100 | 20 | 0 |
| Control | 0 | | |

Preparation of Starting Materials
N,N—Dimethylcarbamimidothioic acid, ethyl ester of the formula $$(CH_3)_2-N-\underset{\underset{SC_2H_5}{|}}{C}=NH$$

can be prepared by the reaction of N,N-dimethylthiourea (O. Wallach, Ber. 32, 1872–75 (1899)) with an ethyl halide, followed by treatment of the N,N-dimethylcarbamimidothioic acid, ethyl ester, hydrogen halide thus formed with a base.

The reaction scheme is as follows:

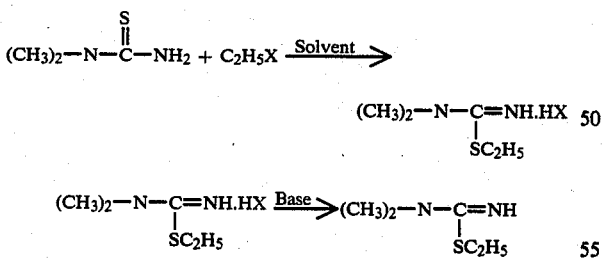

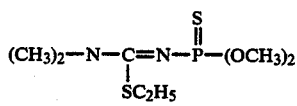

In the above equation, X represents iodo, bromo or chloro.

In carrying out this reaction, a substantially equimolar amount of ethyl halide is slowly added to a mixture of N,N-dimethylthiourea and a solvent, such as, ethanol, methanol or toluene. The mixture is then stirred at a temperature from about 10° to reflux temperature until the reaction is complete (from about 1 hour to approximately 3 days, depending on the ethyl halide and temperature employed). The reaction mixture is heated under reduced pressure to remove most of the solvent leaving the crude N,N-dimethylcarbamidothioic acid, ethyl ester hydrogen halide as oil or crystalline solid.

The N,N-dimethylcarbamimidothioic acid, ethyl ester, hydrogen halide can be treated directly with a base such as, a dilute aqueous sodium or potassium hydroxide solution or if desired, the product can be separated and purified by recrystallization from a solvent, such as ethanol, methanol or the like and then treated with the base to obtain the product as the free base.

EXAMPLE XI

N,N-Dimethylcarbamimidothioic acid, Ethyl Ester, Hydrogen Iodide

A mixture of 156 g of N,N-dimethylthiourea and 400 ml of ethanol was heated to gentle reflux and 250 g of iodoethane was added dropwise. After the addition was complete the mixture was heated under reflux for 2 hours. The solvent was partially removed by distillation under reduced pressure and to the residue diethyl ether was added. The N,N-dimethylcarbamimidothioic acid, ethyl ester, hydrogen iodide separated as white crystals, m.p. 110°–112° in a yield of 366 g (94% of the theoretical).

Analysis: Found: C, 22.66; H, 4.96; N, 10.79. Calculated for $C_5H_{12}N_2S.HI$: C, 23.08; H, 5.04; N, 10.77.

EXAMPLE XII

N,N-Dimethylcarbamimidothioic Acid, Ethyl Ester

To a well stirred mixture of 364 g of N,N-dimethylcarbamimidothioic acid, ethyl ester, hydrogen iodide, 420 ml of ice-water and 560 ml of methylene chloride was added in a slow stream 225 ml of 25% aqueous sodium hydroxide. The temperature during the addition was kept below 5° C. The layers were separated and the aqueous layer extracted twice with methylene chloride. The combined methylene chloride solution was dried over anhydrous sodium sulfate, the solvent removed by distillation under reduced pressure and the residual oil distilled on a small Vigreux column. The fraction boiling at 65° C. at a pressure of 1 millimeter of mercury was collected. N,N-Dimethylcarbamimidothioic acid, ethyl ester is a colorless oil and was obtained in a yield of 162 g (88% of theoretical). The product has a refractive index of $n_d^{25} = 1.5178$. The IR and NMR spectra are in agreement with the assigned structure.

The N'-(Dimethoxyphosphinothioyl)-N,N-dimethylcarbamimidothioic acid, ethyl ester of the following structure $$(CH_3)_2-N-\underset{\underset{SC_2H_5}{|}}{C}=N-\overset{\overset{S}{\|}}{P}-(OCH_3)_2$$

can be prepared by a method wherein substantially equimolar amounts of N,N-dimethylcarbamimidothioic acid, ethyl ester of the formula

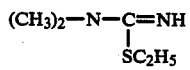

and phosphorochloridothioic acid, O,O-dimethyl ester of the formula

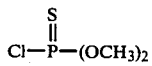

are reacted together in the presence of a solvent and a HCl acceptor.

The reaction scheme is as follows:

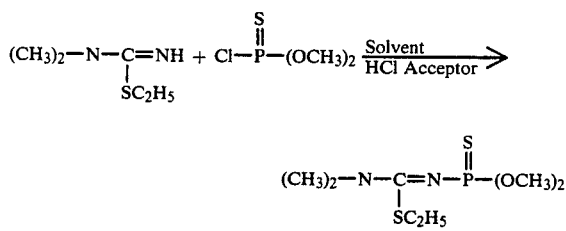

The reaction is conducted in a manner substantially the same as the reaction of Method A, employing temperatures in the range between 15° C. and 80° C. The solvents, the HCl acceptors and the method of recovery are the same as set forth in Method A.

EXAMPLE XIII

N'-(Dimethoxyphosphinothioyl)-N,N-dimethylcarbamimidothioic Acid, Ethyl Ester

To a mixture of 13.2 g of N,N-dimethylcarbamimidothioic acid, ethyl ester, 27.6 g of finely powdered potassium carbonate and 250 ml of acetonitrile, 16.1 g of phosphorochloridothioic acid, O,O-dimethyl ester was added. The mixture was stirred and heated to 40° C. for 4 hours. The salts were removed by filtration and the filtration concentrated in a rotary evaporator. The residue was taken up in methylene chloride, the methylene chloride solution washed thrice with 50 ml portions of water and dried over anhydrous magnesium sulfate. The solvent was removed in a rotary evaporator, leaving 20.0 g of crude product. To remove some lower boiling impurity the sample was placed in a Kugelrohr (bath temperature 95° C., pressure 0.2 mm) for 2 hours. The residue was exhaustively extracted with hexane and the hexane solution concentrated under vacuum, leaving N'-(dimethoxyphosphinothioyl)-N,N-dimethylcarbamimidothioic acid, ethyl ester as a nearly colorless oil. The product has a refractive index of $n_d^{25} = 1.5610$. The IR and NMR spectra were in agreement with the structural assignment.

Analysis: Found: C, 32.42; H, 6.40; N, 10.94. Calculated for $C_7H_{17}N_2O_2PS_2$: C, 32.80; H, 6.69; N, 10.93.

N'-(Dimethoxyphosphinothioyl)-N,N-dimethylcarbamimidothioic acid, ethyl ester can also be prepared by an alternative method wherein substantially equimolar amounts of N,N-dimethylcarbamimidothioic acid, ethyl ester of the formula

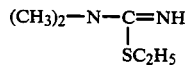

and thiophosphoryl chloride of the formula

are reacted together in the presence of a solvent and a HCl acceptor. The N'-(dichlorophosphinothioyl)-N,N-dimethylcarbamimidothioic acid ethyl ester intermediate of the formula

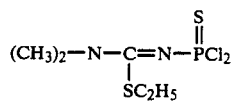

is then allowed to react with methanol in the presence of an HCl acceptor.

The reaction scheme is as follows:

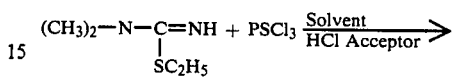

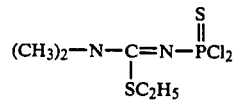

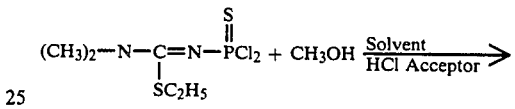

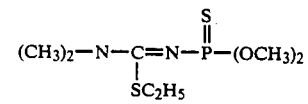

In carrying out this reaction substantially equimolar amounts of N,N-dimethylcarbamimidothioic acid, ethyl ester and a hydrogen chloride acceptor, such as triethylamine, pyridine, an alkali carbonate such as sodium carbonate or potassium carbonate and the like are added together or subsequently to a solution of a substantially equimolar amount of thiophosphoryl chloride in a solvent such as methylene chloride, benzene, toluene, cyclohexane and the like, employing a temperature in the range between −10° C. and −25° C. To this mixture at least 2 moles of methanol and a hydrogen chloride acceptor, such as triethylamine, pyridine, sodium methoxide or an alkali carbonate, such as sodium carbonate or potassium carbonate and the like are added. The reaction is carried out employing a temperature in the range between 0° C. and +80° C. The method of recovery is essentially the same as set forth in Method A.

EXAMPLE XIV

N'-(Dimethoxyphosphinothioyl)-N,N-dimethylcarbamimidothioic Acid, Ethyl Ester

A solution of 33.9 g of thiophosphoryl chloride in 100 ml of methylene chloride was cooled to approximately −5° C. and subsequently 26.4 g of N,N-dimethylcarbamimidothioic acid, ethyl ester and 21 g of triethylamine were slowly added. The mixture was then allowed to attain room temperature and was kept at this temperature for one hour. To this mixture, 100 ml of methanol was added, followed by a dropwise addition of 44 g of triethylamine. The mixture was then stirred for approximately 30 hours. Precipitated triethylamine hydrochloride was removed by filtration and the filtrate was concentrated under vacuum. Methylene chloride was added to the residue and the mixture was washed thrice with water, once with 5% aqueous sodium hydroxide and the methylene chloride solution dried over anhydrous magnesium sulfate. The solvent was removed in a rotary evaporator leaving 48.2 g (94% of theoretical) of N'-(dimethoxyphosphinothioyl)-N,N-dimethylcarbamimidothioic acid methyl ester. The product is a colorless oil and has a refractive index of $n_d^{25}=1.5606$.

Analysis: Found: C, 32.91; H, 6.41; N, 11.00. Calculated for $C_7H_{17}N_2O_2PS_2$: C, 32.80; N, 6.69; N, 10.93.

What is claimed is:

1. A method for the kill and control of insects which comprises contacting said insects or their habitat with a composition which comprises an inert carrier in intimate admixture with an insecticidally effective amount of the active compound of the formula

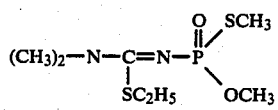

2. A compound of the formula

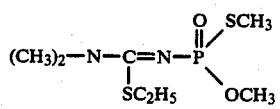

3. An insecticidal composition comprising an inert carrier in admixture with an insecticidally effective amount of the active compound of the formula

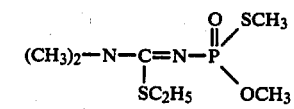

4. A compound of the formula

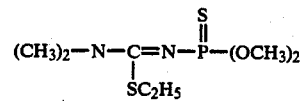

* * * * *